United States Patent [19]

Robison et al.

[11] Patent Number: 4,874,044

[45] Date of Patent: Oct. 17, 1989

[54] METHOD FOR OIL RECOVERY USING A MODIFIED HETEROPOLYSACCHARIDE

[75] Inventors: Peter D. Robison, Poughkeepsie; Arthur J. Stipanovic, Wappingers Falls, both of N.Y.

[73] Assignee: Texaco Inc., White Plains, N.Y.

[21] Appl. No.: 256,014

[22] Filed: Oct. 11, 1988

[51] Int. Cl.$^4$ .................. C08B 37/00; C12P 19/04; E21B 43/22

[52] U.S. Cl. .................. 166/275; 166/246; 252/8.554; 435/101; 435/104

[58] Field of Search .............. 166/246, 273, 274, 275; 435/101, 104; 536/114; 252/8.554

[56] References Cited

U.S. PATENT DOCUMENTS

| | | | |
|---|---|---|---|
| 4,182,860 | 1/1980 | Naslund et al. | 435/104 X |
| 4,245,046 | 1/1981 | Demain et al. | 435/104 |
| 4,286,059 | 8/1981 | Kang et al. | 435/101 |
| 4,440,225 | 4/1984 | Holzwarth | 166/246 |
| 4,466,889 | 8/1984 | Miller et al. | 166/246 |
| 4,481,294 | 11/1984 | Downs | 435/101 X |
| 4,647,657 | 3/1987 | Wan | 536/114 X |
| 4,754,809 | 7/1988 | Van Zanten et al. | 166/246 |

*Primary Examiner*—George A. Suchfield
*Attorney, Agent, or Firm*—Robert A. Kulason; James J. O'Loughlin; Vincent A. Mallare

[57] ABSTRACT

A process for recovering hydrocarbons from a subterranean hydrocarbon bearing formation penetrated by an injection well and a production well which comprises injecting an aqueous drive fluid into the formation and forcing the drive fluid through the formation to recover the hydrocarbons from the production well.

4 Claims, No Drawings

METHOD FOR OIL RECOVERY USING A MODIFIED HETEROPOLYSACCHARIDE

BACKGROUND OF THE INVENTION

This invention is related to the recovery of oil from a hydrocarbon-bearing subterranean formation by injection of a water-soluble polymer in an aqueous solution into the oil reservoir to stimulate additional production and recovery of hydrocarbons. More specifically, the polymer employed is a modified heteropolysaccharide produced by the bacterium Xanthobacter sp.

Generally, oil or hydrocarbons are recovered from subterranean formations BY initially employing primary recovery techniques. Once primary production is no longer economically feasible, some form of enhanced recovery is applied to these formations to abstract further quantities of oil. One of the earliest and most popular forms of enhanced oil recovery is water injection in which water or brine is injected into the hydrocarbon containing formation to force the residual hydrocarbons contained therein through the formation to a production well which is placed at an appropriate location. Since the viscosity of the hydrocarbons present in the hydrocarbon bearing formation is usually higher than the viscosity of water or other fluids injected into the formation, the quantity of hydrocarbons removed by such methods is small and further, frequently results in the bypassing of a substantial portion of the hydrocarbons by the less viscous water. This effect is referred to as viscous fingering. This situation is further aggravated by the presence of zones of high permeability at various levels in the hydrocarbon bearing formation. These so-called "thief" zones also permit the escape of a substantial portion of the relatively low viscosity water or brine without any displacement of hydrocarbons.

Other problems have arisen in the use of water-soluble bacterial polysaccharides for enhanced oil recovery since the viscous injection fluid (2–2000 cps) is often a diluted fermentation broth (0.01–1.0% w/v) which may contain residual cell bodies, digested solid nutrients and polymer aggregates (microgels). For most polysaccharides, aggregation is exacerbated by the elevated concentrations of mono-, di- and trivalent cations found in reservoir brines which may form specific ionic complexes between polymer chains and/or may generally reduce the "solvent power" of the aqueous media allowing the polymer to readily self-associate. The operational result of aggregation is to reduce the injection rate and increase the injection pressure required to introduce the polymer solution into the subterranean oil reservoir. Further, in some extreme cases, polymer molecules aggregated into networks may cause plugging in the porous reservoir rock matrix which could ultimately result in permanent damage to the formation. In the present invention, the ability to inject a heteropolysaccharide into a hydrocarbon-containing reservoir is significantly improved by including the compound beta-fluoropyruvate in the fermentation medium of the organism Xanthobacter sp. This effect is especially pronounced at elevated salinity.

Thus, it is an object of the present invention to provide an improved process for recovering hydrocarbons from subterranean hydrocarbon bearing formation.

Also, it is an object of the present invention to provide an improved additive, i.e., drive fluid, for enhancing the recovery of such hydrocarbons.

DISCLOSURE STATEMENT

U.S. Pat. Nos. 2,827,964 and 3,039,529 disclose a method of improving the efficiency of enhanced recovery techniques through the addition of a substance to the water or brine to increase its viscosity and describe the use of high molecular weight, partially hydrolyzed polyacrylamides as thickening agents for aqueous fluids employed in enhanced oil recovery systems.

U.S. Pat. No. 3,581,824 describes the use of a heteropolysaccharide produced by bacterial fermentation of carbohydrates for the same purpose as that of U.S. Pat. Nos. 2,827,964 and 3,039,529.

U.S. Pat. No. 4,548,268 discloses a process for recovering hydrocarbons from a subterranean hydrocarbon bearing formation penetrated by an injection well and a production well and includes the steps of injecting into the formation via an injection well an aqueous drive fluid comprising water and more than about 200 parts per million of Beta-(1-6)-D-glucan having an average molecular weight of more than about $2 \times 10^4$.

The process also includes using a concentrate of the glucan in dimethylsulfoxide or in a four molar or higher concentration of aqueous urea which is diluted to form the aqueous drive fluid.

SUMMARY OF THE INVENTION

This invention discloses a new, novel heteropolysaccharide polymer produced by Xanthobacter sp. (Strain NW11, ATCC# 53272) after modification of the polymer by the addition of beta-fluoropyruvate to the fermentation medium. This modification improves the filterability of the polymer and, thus, potential reservoir injections to a point where high levels of salt can be tolerated.

DETAILED DESCRIPTION OF THE INVENTION

NW11 was isolated from a sample from a waste-water pond in Fountainhead, Okla. It is a gram negative, non-sporeforming, non-motile short rod which forms yellow, mucoid colonies. It was identified as Xanthobacter sp. by the American Type Culture Collection in Rockville, Md.

The heteropolysaccharide is produced in 500 ml flasks at 30° C. after 5–7 days of rotary shaking at 200 rpm. The medium (100 mls) contains 1.75 g glucose, 0.5 g K1HP04, 0.02 g MgSO4 and either 1.4 g Corn Steep Liquor or 0.3 g Bacto-Peptone. Good growth and polymer production by the organism is obtained using either source (Table I). Tryptone and enzyme hydrolyzed casein can also be used.

TABLE I

| GROWTH AND POLYMER PRODUCTION BY NW11 | | |
|---|---|---|
| Medium | Broth Viscosity (cps) | % Solids* |
| Corn Steep Liquor | 3000 | 1.04 |
| Bacto-Peptone | 3600 | 0.95 |

*Amount of polymer as measured by isopropanol-precipitable material

When beta-fluoropyruvate (BFPyr) was used, it was added to the medium in a sterile, concentrated aqueous solution. Growth of the organism is inhibited by BFPyr so this was minimized by adding it after 6–12 hours.

The polymer from NW11 contains the sugar glucose, glucuronic acid and mannose in a 2-1-1 ratio. It also contains acetate at a level of less than one per 4 sugar repeat unit.

After the fermentation the broth is adjusted to pH=7.0 and autoclaved for 20 minutes in a stoppered tube. This results in maximum viscosity. Autoclaving does not have an affect on the filterability.

In an oil recovery process, it is important to determine the ability to inject a polymer containing aqueous drive fluid into a subterranean hydrocarbon bearing formation through an injection well without excessive pressure buildup due to pore plugging. Drive fluids formed from many polymers such as xanthum gum may contain microgels, as well as residual dead bacterial cell bodies. Such materials often give rise to poor injectability due to the plugging of the area near the well bore.

Injectivity of polymer solutions into formations can be correlated with a simple laboratory filterability test. In this test, a dilute solution (viscosity about 20 cps) of the polymer is passed through a Nucleopore membrane of 47 mm diameter and 3.0 u pore size. Pressure is held at 20 psi and the flow rate is monitored. The time necessary to accumulate a given volume of filtrate is measured and a filter factor (FF) is calculated according to the following formula.

$$\text{Filter Factor} = \frac{\text{time of 300 ml accumulation} - \text{time 200 ml}}{\text{time 200 ml} - \text{time 100 ml}}$$

Values greater than about 2 indicate filter plugging and are unacceptable. Samples for which 300 mls of filtrate cannot be collected after about 600 seconds are also considered unacceptable.

Often a polymer will have acceptable filterability in water or low salt levels but upon increasing the salt the filter factor will rise above 2 and be said to fail. The maximum salt concentration at which the filterability is acceptable is called the critical salinity (C*) and is measured in units of percent NaCl.

The present invention and the advantages provided by such will be more apparent by the examples provided below.

EXAMPLE 1

NW11 was grown in peptone medium and the broth was diluted to a viscosity of about 20 cps. The filterability was tested in water, 2 percent and 4 percent NaCl. The results (Table II) show that the polymer passes the filterability test in H$_2$O, is marginally acceptable in 2 percent NaCl (the filter factor is very close to 2) and is unacceptable in 4 percent NaCl. The C* of this sample is 2. For the 4 percent NaCl filtrate, less than 300 mls were collected in 600 seconds. The filter factor generally increases very rapidly when C* is exceeded.

TABLE II
FILTERABILITY OF NW11 IN PEPTONE MEDIUM

| Solution | Filter Factor |
| --- | --- |
| H$_2$O | 1.2 |
| 2% NaCl | 2.3 |
| 4% NaCl | >10 |

EXAMPLE II

Three flasks of NW11 were grown in peptone medium. One flask remained unmodified as the control. BFPyr at levels of 0.2 mM and 0.6 mM were added to the other two flasks just before inoculation of the organism. After 7 days of growth, the broths of each flask were diluted to 20 cps and the filterability tested. The results are shown in Table III. C* in the 0.2 mM flask was raised from 2 to 4 and with the higher BFPyr flask to 6.

TABLE III
FILTERABILITY OF BFPyr MODIFIED NW11

| Filter Factor Sample | H2O | 2% NaCl | 4% NaCl | 6% NaCl | 8% NaCl |
| --- | --- | --- | --- | --- | --- |
| Control | 1.18 | 1.34 | >10 | — | — |
| 0.2 mM BFPyr | 1.09 | 1.55 | 2.04 | >10 | — |
| 0.6 mM BFPyr | 1.38 | 1.51 | 1.60 | 1.67 | >10 |

EXAMPLE III

Two flasks of NW11 were grown in peptone medium. One flask remained unmodified as the control. BFPyr at a level of 0.6 mM was added to the other flask just before inoculation of the organism. After 7 days of growth, the broths of each flask were diluted to 20 cps and the filterability tested. The C* of the control flask was 2 and the BFPyr-treated flask was 6. The polysaccharide was purified from the cells. The acetate levels were determined by a KOH hydrolysis followed by HPLC analysis. NW11 polymer from the control flask had a level of 5.7 percent and the BFPyr flask was 7.8 percent. This indicates that the improvement of filterability may be due to an increase in the acetate level of the polymer.

EXAMPLE IV

Four flasks of NW11 were prepared in peptone medium. One flask remained unmodified as the control. To the other three, 0.6 mM BFPyr was added either before inoculation, after 7 hours of growth, or after 12 hours of growth. Growth in the flask (as measured by absorbance) in which the BFPyr was added at time 0 was greatly inhibited, the flask with the 7 hour addition less so and the 12 hour flask was only inhibited slightly (Table IV). The amount of polymer production at the end of 7 days, as measured by percent isopropanol precipitable material, was only slightly reduced as compared to the control and not much different from each other.

TABLE IV
EFFECT OF BFPYR ON GROWTH AND POLYMER PRODUCTION OF NW11

| Sample | OD 600 at 24 hrs | OD 600 at 48 hrs | % Solids |
| --- | --- | --- | --- |
| Control | 3.10 | 7.03 | 0.83 |
| 0.6 mM BFPyr added at | | | |
| 0 hours | 0.22 | 0.82 | 0.57 |
| 7 hours | 0.64 | 2.11 | 0.61 |
| 12 hours | 2.25 | 6.93 | 0.65 |

EXAMPLE V

Six flasks of NW11 were prepared in peptone medium. One flask remained unmodified as the control. To the other five, varying amounts of BFPyr from 0.6 to 3.0 mM were added after 7 hours of growth. The higher the amount of BFPyr, the more polymer production was inhibited, as measured by broth viscosity and percent solids (Table V). Filterabilities of each flask in increasing salt concentrations were performed. The C* increased from 0 in the control to 9 percent NaCl at 1.8 mM but did not increase at higher levels of BFPyr. This indicates that 1.8 mM BFPyr is optimum for increase in C* with minimum inhibition of growth.

TABLE VI

EFFECT OF BFPYR CONCENTRATION ON NW11

| Sample After 7 days | Broth Viscosity (cps) | % Solids | C* % NaCl |
|---|---|---|---|
| Control | 1900 | 0.65 | 0 |
| BFPyr | | | |
| 0.6 mM | 1700 | 0.64 | 5 |
| 1.2 mM | 1400 | 0.57 | 7 |
| 1.8 mM | 1000 | 0.49 | 9 |
| 2.4 mM | 900 | 0.46 | 9 |
| 3.0 mM | 800 | 0.40 | 9 |

EXAMPLE VI

Samples of NW11 broth usually contain extracellular protein as well as polysaccharide. Three flasks of NW11 grown for 7 days in peptone medium were prepared. Three flasks of NW11 in which 1.8 BFPyr was added after 7 hours were also prepared. Each batch of 3 flasks was combined, autoclaved and purified polysaccharide prepared. This was accomplished by diluting the sample 10 fold, ultracentrifuging for 2 hours at 50,000 xg, precipitating 3–4 times with isopropanol and dialyzing extensively against water. This series of steps was carried out 2–3 times. Final samples containing less than 0.5 percent protein were obtained for the NW11 control sample and less than 2 percent protein for the BFPyr modified sample. Solutions of about 20 cps were made up for both and filterabilities performed. The NW11 control had a C* of 0 percent NaCl and the BFPyr-modified sample had a C* of 6 percent NaCl. Therefore the improvement in filterability for NW11 by BFPyr is due to an effect on the polysaccharide and not the extracellular protein.

It is pointed out that the scope of the present invention is determined by the following claims and is not to be considered part of the prior art.

We claim:
1. A process for recovering hydrocarbons from a subterranean hydrocarbon bearing formation penetrated by an injection well and a production well which comprises:
    (a) injecting into the formation via said injection well an aqueous drive fluid comprising water and more than 50 ppm of a beta-fluoropyruvate modified NW11 heteropolysaccharide;
    (b) forcing said aqueous drive fluid through the formation and
    (c) recovering hydrocarbons from said production well.
2. A process for producing a heteropolysaccharide comprising:
    (a) inoculating Xanthobacter sp. strain NW11-ATCC 53272 into an aqueous fermentation medium containing a carbon and nitrogen source;
    (b) adding from 0.3 to 3.0 mM beta-fluoropyruvate to the fermentation after 0 to 24 hours;
    (c) incubating said inoculated material at a temperature ranging from 26° to 30° C. for a period of about 120 to about 170 hours to form a heteropolysaccharide and
    (d) recovering the polysaccharide.
3. The heteropolysaccharide produced in claim 2 wherein said heteropolysaccharide has an acetate level of at least 7 percent.
4. The method of claim 2 wherein said carbon-containing material is selected from the group consisting of glucose, xylose, fructose, arabinose, mannose, lactose, maltose and sucrose and the nitrogen source is selected from the group consisting of peptone, corn steep liquor, tryptone and enzyme-hydrolyzed casein.

* * * * *